United States Patent [19]

Tunney

[11] Patent Number: Plant 6,228

[45] Date of Patent: Jul. 19, 1988

[54] ROSEBUD MAPLE

[76] Inventor: Thomas G. Tunney, Star Rte. 2, Iron Mountain, Mich. 49801

[21] Appl. No.: 846,367

[22] Filed: Mar. 31, 1986

[51] Int. Cl.[4] ..... A01H 5/00

[52] U.S. Cl. ..... Plt./51

[58] Field of Search ..... Plt./51

*Primary Examiner*—Robert Bagwill

*Attorney, Agent, or Firm*—Robert G. Mentag

[57] ABSTRACT

A Norway Maple tree having new foliage of a red** color, turning dark green* with maturity.

3 Drawing Sheets

1

This specification relates to a new and distinct variety of Norway Maple (Acer platanoides) tree. The variety name is Rosebud Maple.

The new variety was discovered in a group of Norway Maple (Acer platanoides) seedlings planted for shade tree production in the Pine Mountain Nurseries, Iron Mountain, Mich. Its origin is not known or traceable by the grower of the seedlings.

In early spring the new variety has the appearance of Norway Maple (Acer platanoides) with dark green* leaves. (*spinach green, chart No. 960, from The "Royal Horticultural Society Color Chart") By mid-spring all new end growth leaves and stems bud forth in a red color, (Chrysanthemum crimson, chart No. 824, from The "Royal Horticultural Society Color Chart") with this color holding through the entire growing season until autumn coloration or defoliation causes change. Throughout the growing season, the red** terminal growth gives a flowering appearance among the dark green* leaves.

As is well known, Norway Maple (Acer platanoides) is grown for its wood, its ornamental value and shade in landscape plantings, and for its ability to withstand drought and city conditions.

This discovery provides a new variety of the Norway Maple (Acer platanoides) tree for use as an ornamental and shade tree in landscape planting. The distinctive red** terminal growth among the dark green* leaves adds a new dimension to the use of shade trees in the color scheme of home, commercial and public site development.

Figure 1:
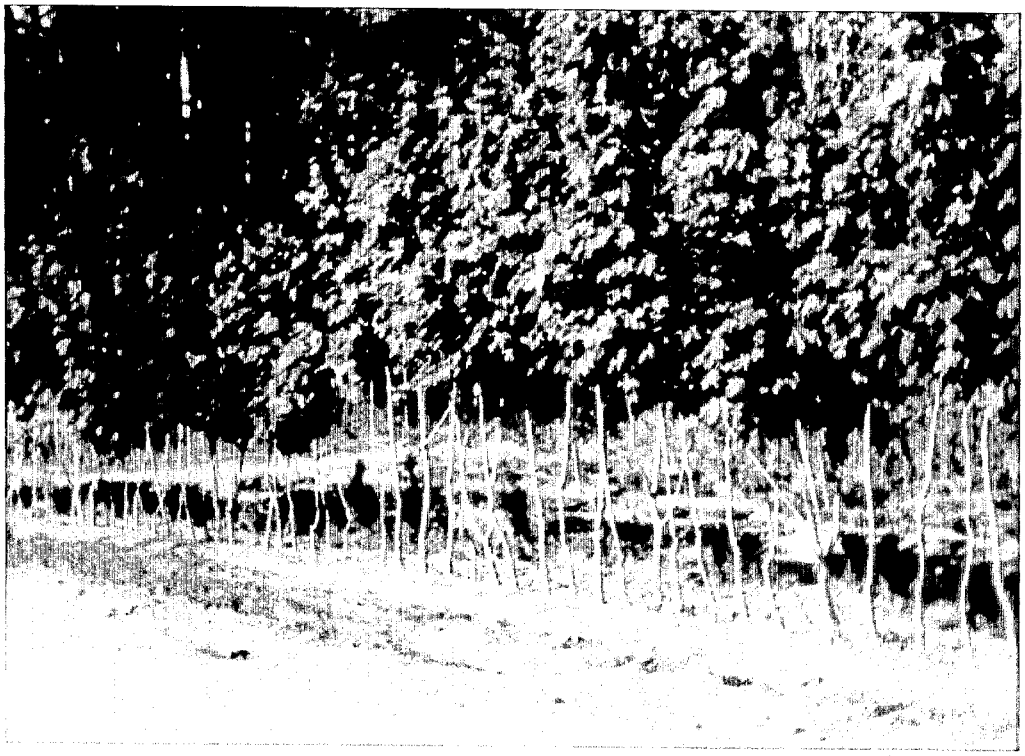
Figure 2:
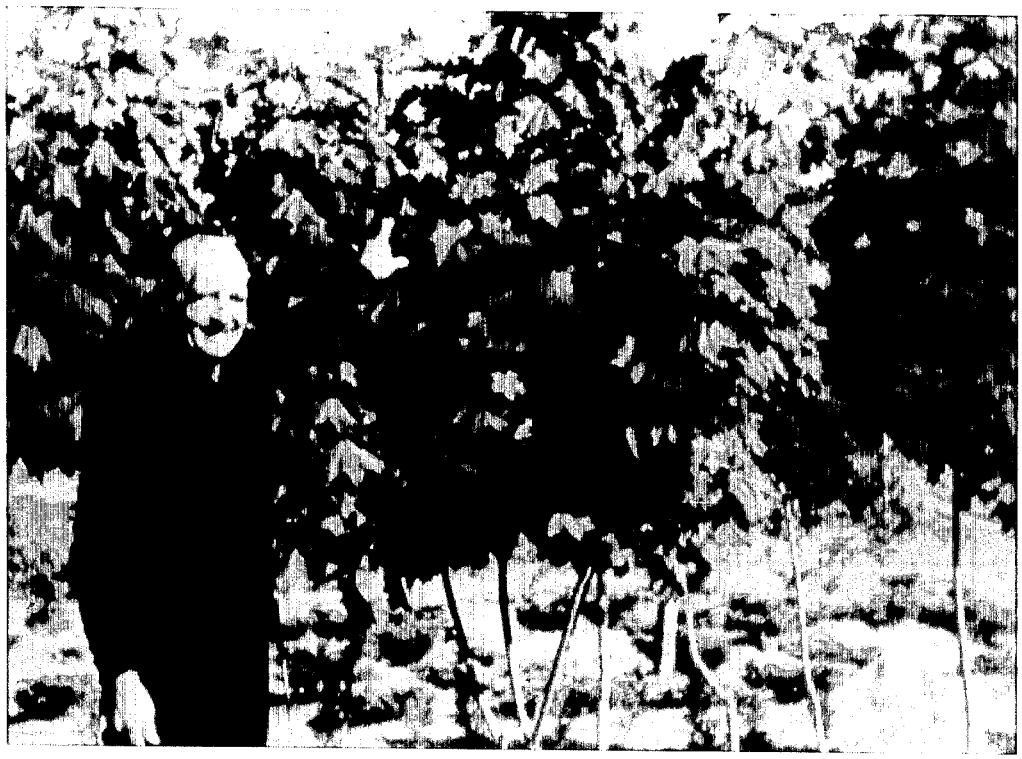
Figure 3:
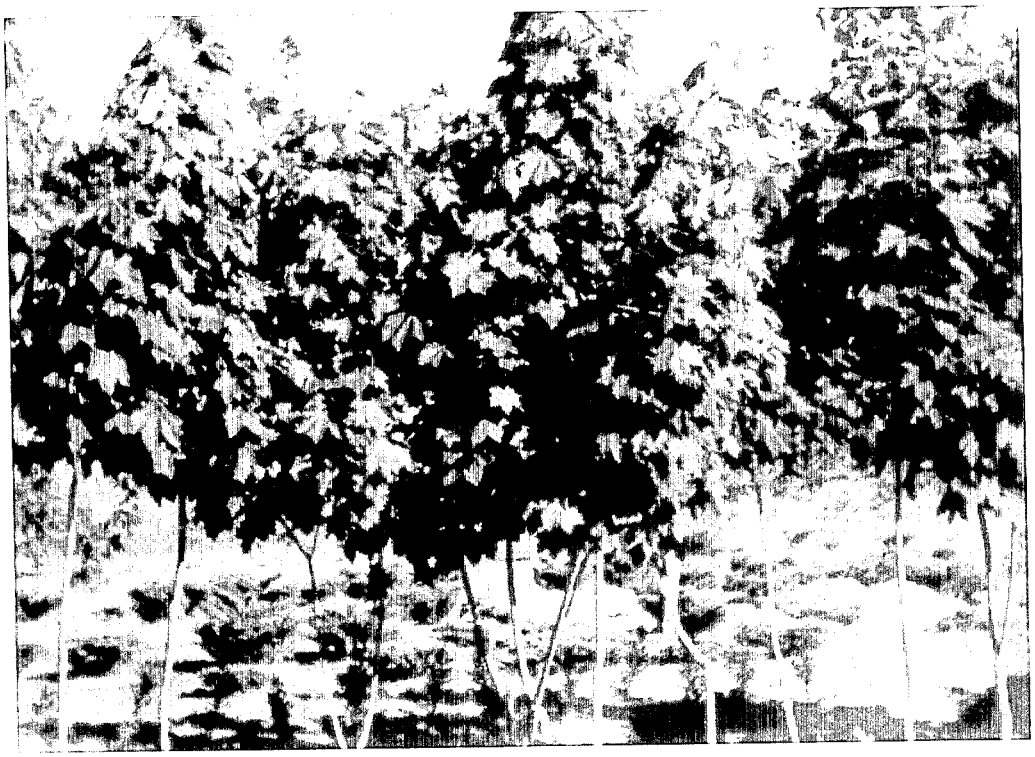
Figure 4:
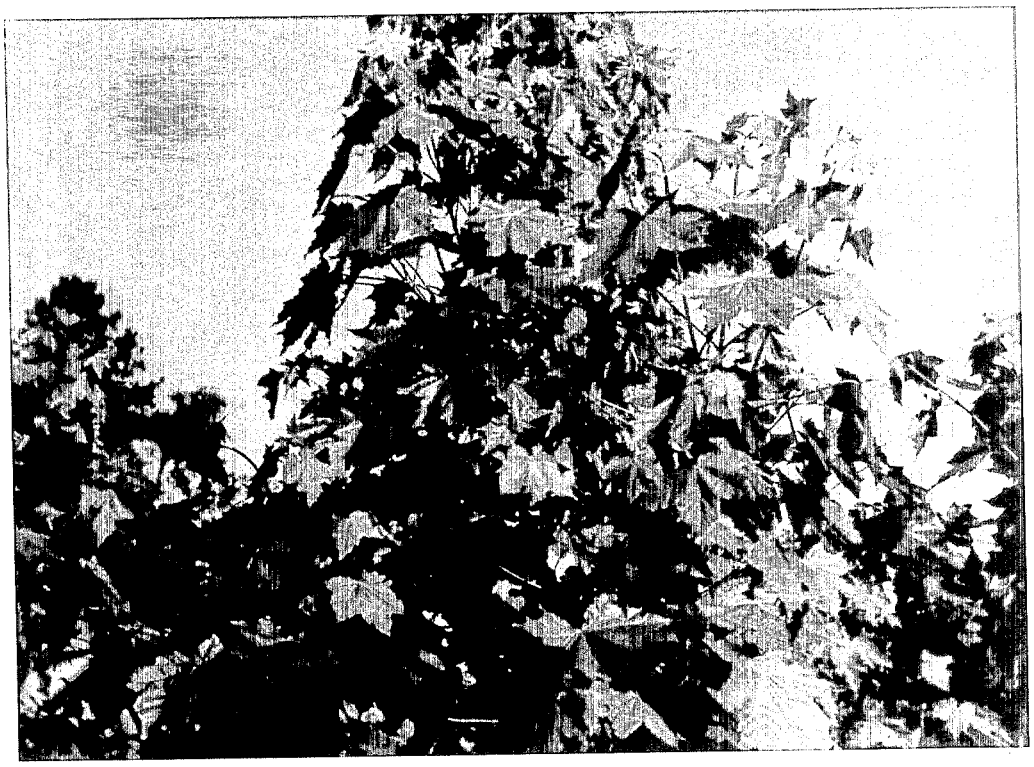
Figure 5:
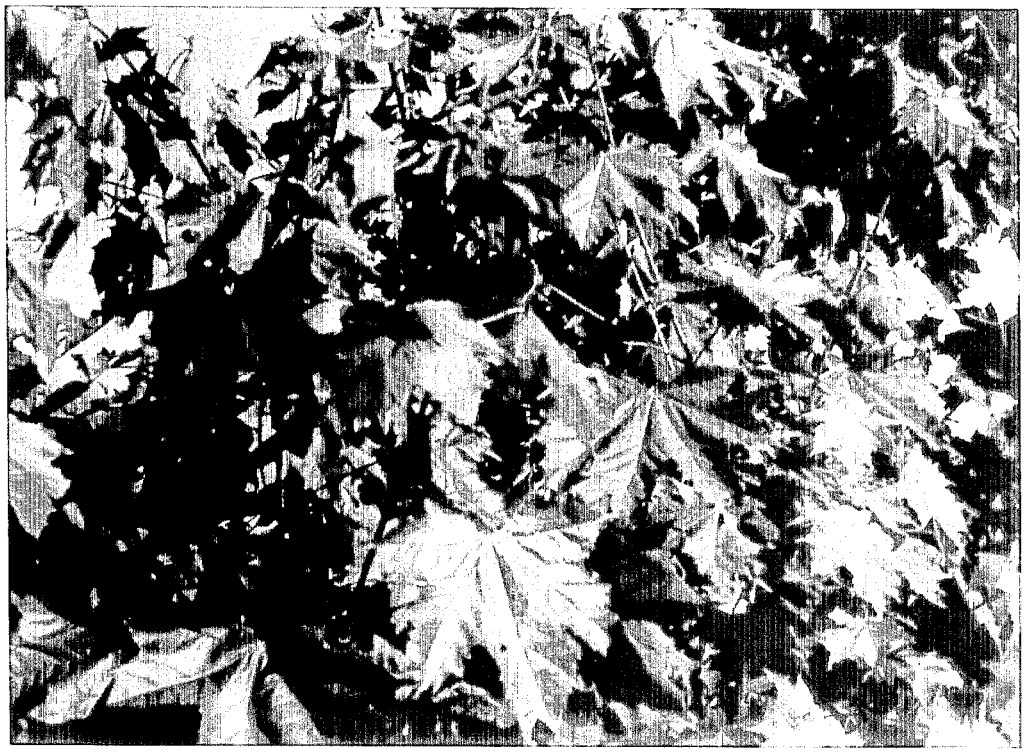

Supporting evidence for the colors and shape of the leaves, and the new end growth leaves and stems is furnished in the five color photographs, which comprises FIGS. 1 through 5 of the drawings. The trees in these Figures are 8 years old, and they vary in height from 9 feet to 10 feet.

2

The following are the directly observable characteristics of the discovery:

LEAVES

The leaves are 5 lobed, cordate at base, glabrous. The terminal leaves are red**. The lobes are pointed, remotely dentate and with pointed teeth.

STEMS

The stems in the early leafing stage are red**, holding through the entire growing season.

WOOD

The density of the wood appears to be the same as for other Norway Maple (Acer platanoides) trees.

FLOWERS

No flowers have been observed thus far.

RESISTANCE TO DISEASE

No known diseases or disease symptoms have been observed.

REPRODUCTION

The tree has been reproduced by sicon and bud grafting on Acer Saccharum stock.

GROWTH RATE

The caliper of 78 of the new variety Norway Maples (Acer platanoides) in the 9th year is an average of 1½"–3". From the 8th to 9th year the growth rate averages 2–2½ ft.

I claim:

1. The Norway Maple (Acer platanoides) tree herein described characterized by the red** key terminal growth holding through the entire growing season.

* * * * *